(12) United States Patent
Picker

(10) Patent No.: US 11,325,003 B2
(45) Date of Patent: May 10, 2022

(54) ATHLETIC TRACKING DEVICE

(71) Applicant: Melissa Picker, St. James, MO (US)

(72) Inventor: Melissa Picker, St. James, MO (US)

( * ) Notice: Subject to any disclaimer, the term of this patent is extended or adjusted under 35 U.S.C. 154(b) by 432 days.

(21) Appl. No.: 16/668,171

(22) Filed: Oct. 30, 2019

(65) Prior Publication Data
US 2021/0128977 A1 May 6, 2021

(51) Int. Cl.
| | |
|---|---|
| *G06F 3/048* | (2013.01) |
| *A63B 24/00* | (2006.01) |
| *A61B 5/024* | (2006.01) |
| *A61B 5/00* | (2006.01) |
| *A63B 71/06* | (2006.01) |
| *G06F 1/16* | (2006.01) |
| *G16H 20/60* | (2018.01) |
| *G06F 3/04817* | (2022.01) |
| *G06V 10/426* | (2022.01) |

(52) U.S. Cl.
CPC ...... *A63B 24/0062* (2013.01); *A61B 5/02438* (2013.01); *A61B 5/681* (2013.01); *A63B 71/0622* (2013.01); *G06F 1/163* (2013.01); *G06F 3/04817* (2013.01); *G06V 10/426* (2022.01); *G16H 20/60* (2018.01); *A63B 2071/0625* (2013.01); *A63B 2071/0655* (2013.01); *A63B 2071/0663* (2013.01); *A63B 2220/17* (2013.01); *A63B 2225/20* (2013.01); *A63B 2230/06* (2013.01)

(58) Field of Classification Search
CPC ........................ A63B 24/0062; A63B 71/0622; G16H 20/60; G06V 10/426; A61B 5/02438; A61B 5/681; G06F 1/163; G06F 3/04817
See application file for complete search history.

(56) References Cited

U.S. PATENT DOCUMENTS

| 10,776,739 | B2 * | 9/2020 | Blahnik | G06Q 30/0207 |
| 11,083,396 | B2 * | 8/2021 | Sano | A61B 5/681 |
| 11,152,100 | B2 * | 10/2021 | Crowley | G06F 1/163 |
| 11,209,957 | B2 * | 12/2021 | Dryer | G06F 3/04847 |
| 11,216,119 | B2 * | 1/2022 | De Vries | G06F 3/0485 |

(Continued)

*Primary Examiner* — David Phantana-angkool
(74) *Attorney, Agent, or Firm* — Bruce A. Lev

(57) ABSTRACT

An activity tracking device for tracking and incentivizing personal goals. One embodiment of the activity tracking device is formed as a fitness smart watch with sliders for tracking water and fruit/vegetable intakes, and with the typical smart watch features, including a pedometer, heart-rate monitor, altimeter, stop watch, vibrating notifications, alerts, etc. Another embodiment of the activity tracking device is formed as a band that would have no automated tracking, however users could choose from different bands for tracking their goals for various activities like drinking enough water, fruit and vegetable intake, daily exercises, meditation breaks during the day and more. A preferred embodiment of the activity tracking device is formed as a computer device having computer application thereon that provides a method of tracking and incentivizing personal goals and provides a plurality of electronic touch screen pages that are adapted to allow a user to create goal monitoring electronic pages that allows the user to input data correlating to the progression towards personal goals, and to which graphic images are created to provide the percent of completion of their goals.

20 Claims, 9 Drawing Sheets

(56) References Cited

U.S. PATENT DOCUMENTS

| | | | | |
|---|---|---|---|---|
| 2006/0184409 A1* | 8/2006 | Bangel | ............... | G06Q 10/0637 |
| | | | | 705/7.42 |
| 2008/0109257 A1* | 5/2008 | Albrecht | ................ | G16H 50/20 |
| | | | | 600/300 |
| 2012/0290979 A1* | 11/2012 | Devecka | ............ | G06Q 30/0255 |
| | | | | 715/810 |
| 2012/0301856 A1* | 11/2012 | Quatrochi | ............ | A61B 5/7465 |
| | | | | 434/247 |
| 2014/0276244 A1* | 9/2014 | Kamyar | ................ | A61B 5/1112 |
| | | | | 600/595 |
| 2015/0213203 A1* | 7/2015 | Cumbie | ................. | G16H 10/65 |
| | | | | 705/3 |
| 2016/0058337 A1* | 3/2016 | Blahnik | ................ | A61B 5/1116 |
| | | | | 600/595 |
| 2018/0329584 A1* | 11/2018 | Williams | ........... | A63B 24/0075 |
| 2021/0128977 A1* | 5/2021 | Picker | ..................... | G06F 1/163 |
| 2021/0169417 A1* | 6/2021 | Burton | ................ | A61B 5/4812 |
| 2021/0383718 A1* | 12/2021 | Dilger | .................... | G09F 27/00 |
| 2022/0028529 A1* | 1/2022 | Paull | ................... | A61B 5/7465 |

\* cited by examiner

ATHLETIC TRACKING DEVICE

CROSS-REFERENCE TO RELATED APPLICATION

The present application is related to and claims priority from prior provisional application Ser. No. 62/400,089, filed Sep. 26, 2016, and non-provisional application Ser. No. 15/716,090, which applications are incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CPR 1.71(d).

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. Field of the Invention

The present invention relates generally to the field of athletic and personal goal tracking devices and more specifically relates to an activity tracking device having at least two different models. One model would be a fitness smart watch version with the typical smart watch features, including a pedometer, heart-rate monitor, altimeter, stop watch, vibrating notifications, alerts, etc. However, this smart watch would have a way to count simple daily goals, like the number of breaks taken during the day, the number of servings of fruit or veggies consumed, the number of cigarettes one smoked in a day, the number of times one walked the dog a day, etc. using a watch facing touchscreen for counting towards these custom goals and/or a slider/notch system where a knob/lever can be moved up towards a goal or buttons used for counting towards a goal. In addition, the smart watch would have a related app, where any daily goal that can be reasonably counted towards, a user can create on the app and then count towards on the fitness tracker, such as a goal of so many sets of sit-ups a day or so many hugs a day, etc. The second model is a simple band version that would have few to no smart watch functions; however, users would choose an appropriate band for tracking their goals for various activities like drinking enough water, fruit and vegetable intake, daily exercises, meditation breaks during the day, etc. and one or more buttons or sliders for tracking a goal.

2. Description of the Related Art

Fitbits are activity trackers, wireless-enabled wearable technology devices that measure data such as the number of steps walked, heart rate, quality of sleep, steps climbed, and other personal metrics. The first of these was the Fitbit Tracker. Fitbits and other types of sport/fit watches allow users to set only a few personal goals like number of steps, elevation, and other measurable goals. However, users want to track simple daily goals each day as well without having to write it down in a calendar or on a piece of paper, such as walking the dog so many times day, stretching a couple times day, deep breathing a few times day or praying a certain number of times day, etc. (the list of simple daily goals is endless). The current sport/fit watches do not offer the capability for users to track these simple goals and they do not provide enough motivation to help some users stay on track to accomplish their goals. Therefore, a need exists for a specially designed new kind of fitness tracker that will allow users to create their own custom daily goals and/or choose from a list of common daily goals and track (count towards) these goals directly on the fitness tracker itself. In addition, this specially designed new kind of fitness tracker would allow users to have personally chosen inspirational pictures, like a beloved child or beautiful beach to provide the motivation to reach goals for oneself. Self-recorded, inspirational short videos (flicks or personalized snapchats) would also provide motivation. Individualized mantras and voice text messages can be used to enhance their motivation as well. Other fitness trackers require the users to log in to their phone, find their app, open and log into their app into the related App to log or track any health data is that is not automatically measured. This new specially designed fitness tracker version will allow the user to quickly log this data directly on the watch itself throughout the day, without having to log into the app.

Various attempts have been made to solve the above-mentioned problems such as those found in U.S. Pat. and Pub. Nos. 2016/0077492 to Brown et al.; 2014/0099614 to Hu et al.; U.S. Pat. No. 9,050,488 to Brumback et al.; 2015/0066172 to Chiang Ying Yi and U.S. Pat. No. 8,517,896 to Robinette et al. This art is representative of athletic tracking and goal incentivized devices. None of the above inventions and patents, taken either singly or in combination, is seen to describe the invention as claimed.

Ideally, an athletic tracking device should provide a way to create custom goals, track these goals and provide motivation for reaching those goals and, yet would operate reliably and be manufactured at a modest expense. Thus, a need exists for a reliable athletic tracking device with motivational features to achieve the desired results.

BRIEF SUMMARY OF THE INVENTION

In view of the foregoing disadvantages inherent in the known art, the present invention provides a novel athletic tracking device having motivational features and custom daily goal tracking. The general purpose of the present invention, which will be described subsequently in greater detail, is to provide an athletic and personal goal tracking device having at least two different models and also having motivational features. One model would be a fitness smart watch with app, with the typical smart watch features, including a pedometer, heart-rate monitor, altimeter, stop watch, vibrating notifications, alerts, etc., however, also with sliders, buttons and/or or a watch facing touch screen that can be used for counting towards daily goals, like the number of cups of coffee or servings of sweets one had in a day. This version may also provide a way to motivate users with personal, customer inspirational messages, photos, videos, etc. The fitness tracker app would allow the user to choose from a list of common daily goals or to create their very own personal countable goal, no matter what that goal may be. The second model is a simple band version not linked to an app that would have no typical watch functionality, but, would have only a way of counting simple health goals, such as the number of glasses of water one drinks, with a slider or counter button; however, users would choose an appropriate band for tracking their goals for various activities like drinking enough water, fruit and vegetable intake, daily exercises, meditation breaks during the day and more. The slider can be reset to zero by sliding it back down to zero. The counter button could be reset to zero by holding it down for a short time period or possibly via an app where the counter data may be loaded.

The unique features of this invention will provide the following benefits for consumers everywhere:

Fitness bands and watches that can be customized to create custom goals and create custom pictures, short inspirational self-recorded videos, voice messages and mantras, to provide individualized motivation and to share as motivation with friends. Individuals will find the power to reach their goal in order to reveal and share their personal "Power Pic" (children, mother or father) for whom they reach their goal in honor of each day.

The sliding trackers or buttons or watch facing touch screen selection provides a quick, easy and customizable way for users to track what is important to them each day without having to write it down on a piece of paper or use some kind of complicated app on their phones. It's much quicker to slide a tracker up a notch, multiple times a day than to unlock your phone, search for your app, open your app, log into your app and finally log something over and over again all day. It's also much easier to log a goal directly on a watch via a button or touch screen selection than logging into an app as well.

The power to reveal photos, videos, voice messages when goals are achieved will enhance the motivational levels of users.

The ability to choose a custom "voltage level" or the level of daily automated motivation in the form of photos, videos, and messages.

The ability to request a "power surge" and see a photo or a video, or to hear a voice message when a person needs extra inspiration.

A "power grid of friends" to send/receive motivational photos, videos and voice messages to inspire friends as well.

A "power grid of community sponsors" that can become involved by providing motivational support to encourage a healthy lifestyle within their communities.

A "fundraising power grid" to provide many community fund-raising possibilities.

Sliders, buttons or watch facing touchscreen selection, for tracking the number of glasses of water and the number of fruits and vegetables that are eaten, would be available on certain versions of the watch.

A button on the watch can be used for viewing the number of steps, elevation, heart rate, and other smart watch items.

The date and time are displayed on the watch version.

The watch version would notify users automatically when they reach their goals via a sound or beep and/or having the watch vibrate. The watch version would have all the functionality expected for smart watches, include access to text messages, reminders to keep moving, notification of phone calls, etc.

It provides friend/family/team/group healthy lifestyle motivation by sharing and sending motivational photos, recorded videos and voice message.

It can be a community teaching tool as well.

The watch/app can be a teaching/learning tool as it could send out automatic tips and health advice based on app selections (running/walking/yoga/healthy eating/) as the user progresses towards a goal.

Notifications can be turned on or off and set for once up to several times a day.

A watch version may display a virtual track on the watch face showing where the user currently is in relation to their goal for motivation.

The simplest version provides the user the simplest way of counting and tracking their health goals by just moving a slider or pressing a counter button. This data could be loaded to an app. Resetting the counters to zero by adjusting the slider or holding down the button for a short period of time is also extremely simple. The simplest version could be tied to an app for loading the counter information and resetting of the counters at a specific time each day as well. The user can track any goals one wants with this simple band with a counter.

The present invention holds significant improvements and serves as an improved athletic and personal goal tracking device with motivational features. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, the Athletic Tracking Device is constructed and operative according to the teachings of the present invention.

The various embodiments of the present invention will hereinafter be described in conjunction with the appended drawings, wherein like designations denote like elements.

DETAILED DESCRIPTION

Figure 1:
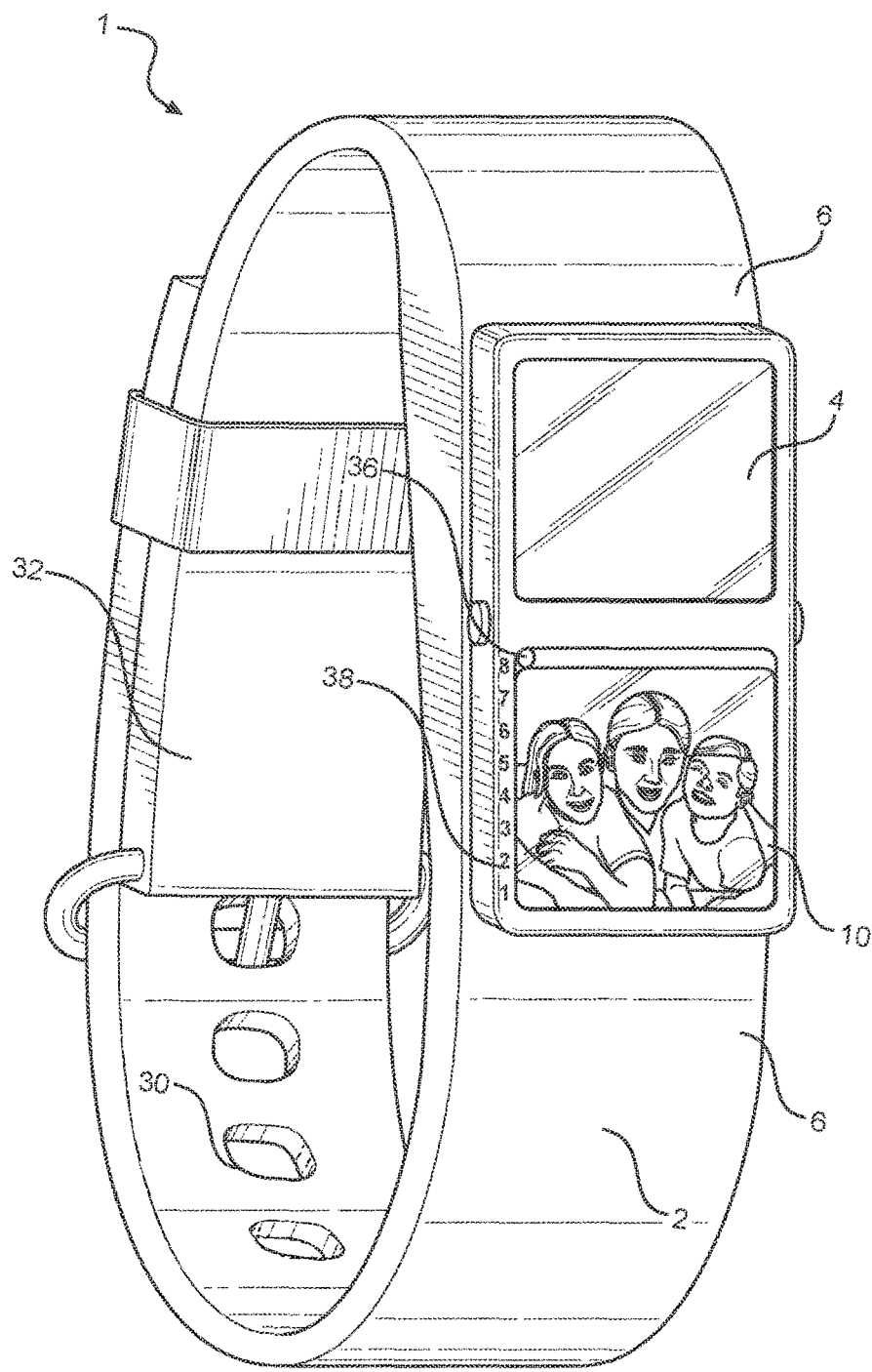
FIG. 1 shows a perspective view illustrating an athletic tracking device with the handle member pushed up (goal reached) and showing an inspirational photograph according to an embodiment of the present invention.

Referring now to the drawings by numerals of reference there is shown in FIGS. 1-5, the athletic tracking or personal goal device 1 is preferably manufactured in several different versions of fitness watches, bands, and smart devices available to accommodate individual needs and budgets. Both the watch versions and bands would have adjustable clasps so they will fit securely around a person's wrist and they will be available in a variety of colors and color combinations to appeal to users. As discussed above, embodiments of the present invention relate to an athletic tracking device 1 having at least two different models as used to improve the tracking of athletic progress.

Figure 3:
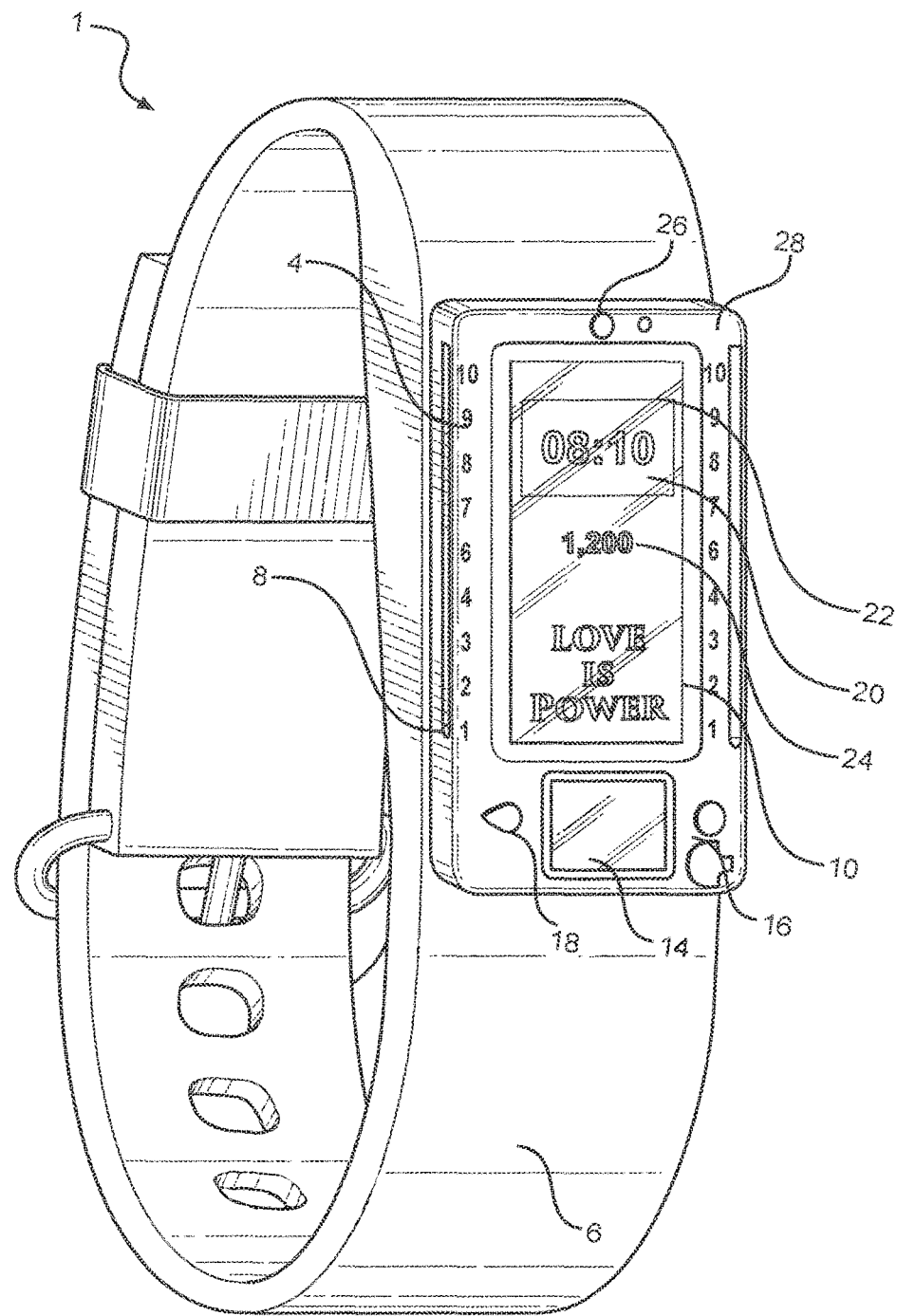
FIG. 3 is a perspective view illustrating the watch version of an athletic tracking device showing various monitors and the slider system where a goal can be counted towards by sliding an entity up one notch at a time as one works towards a goal.

The Power Pic Set Up:

For the watch version of the athletic tracking device 1, as best seen in FIG. 3, the images 10 including Power pics (photos), the inspirational videos (flicks), and voice messages would be recorded and uploaded via the app linked to the watch. Individuals could record and upload a short video for themselves through the app, which will be displayed when reaching their goals. In addition, typed messages could be created and uploaded via the app for display as well.

Figure 4:
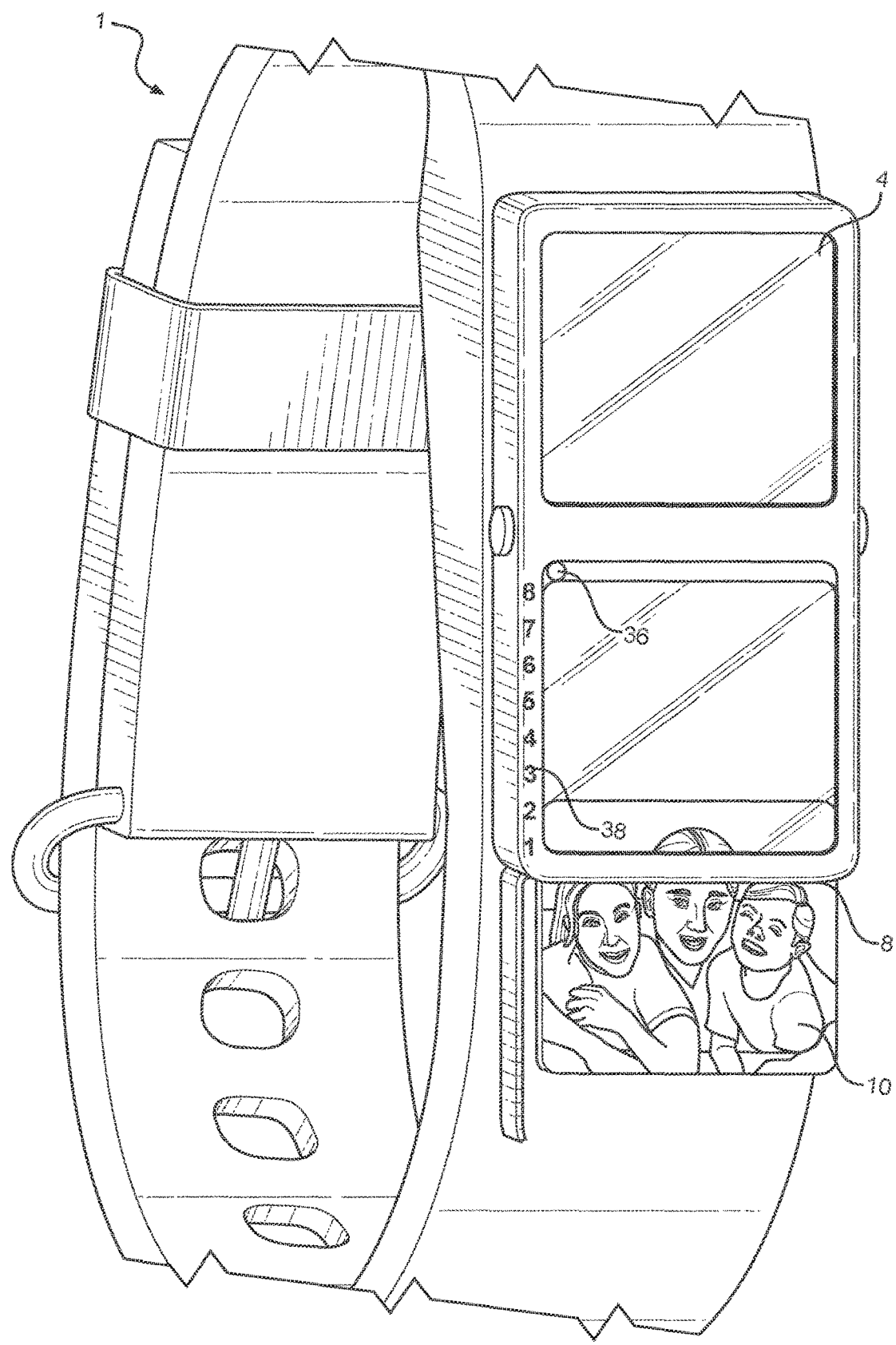
FIG. 4 is a perspective view illustrating a close up of the band version of an athletic tracking device according to an embodiment of the present invention of FIG. 1.

For the band version of the athletic tracking device 1, the Power photo (Pic) image 10 is manually inserted into the watch as best seen in FIG. 4.

The Power Pic Reveal & "Voltage Level":

For the watch version, best seen in FIG. 3, of the athletic tracking device 1, as a user is gradually making their goal, images 10 including the power pics (photos), videos (Flicks-like snapchats) and messages are revealed in various ways, by previously made selections on the app linked to the athletic tracking device 1. A Power Pic is revealed gradually as one gets closer to a goal, such as pieces of a picture gradually being revealed until the goal is reached and the full Power Photo is seen, or being revealed in a "ring-like" fashion or like paint being peeled back to reveal the full photo or video . . . the possibilities are endless. Through the app, users would be able to choose an image 10 including a single photo, video or message to reveal each day or multiple of these depending on the level of needed inspiration that the user desires.

For the watch version of the athletic tracking device 1, as seen in FIG. 3, to help keep users motivated through the day, users would have the option to reveal some images 10 including photos, videos or messages as they make progress and reach a certain percentage of their goal. In this case, the images 10 including power pic, videos, and messages would be like "volts" of power to help keep one inspired. Another option would be to choose to ONLY see the special Power Pic, video, or message images 10 once they reach their goal. These levels of options could be known as a "voltage level" and it could all be set and customized in the app.

For the watch version of the athletic tracking device 1, as seen in FIG. 3, individuals would be allowed to customize how much inspiration or inspiration or daily volts one needs. The photos, videos, and message images 10 would rotate through in a specific order or are selected randomly, to reveal a surprise each day or when a goal is achieved. Bonus photos, video images, and voice message images 10 may be displayed when users surpass their goals, such as when they reach their goals five times in one week or go past their goals by 10%, with the parameters for the bonus items defined in the app.

Figure 2:
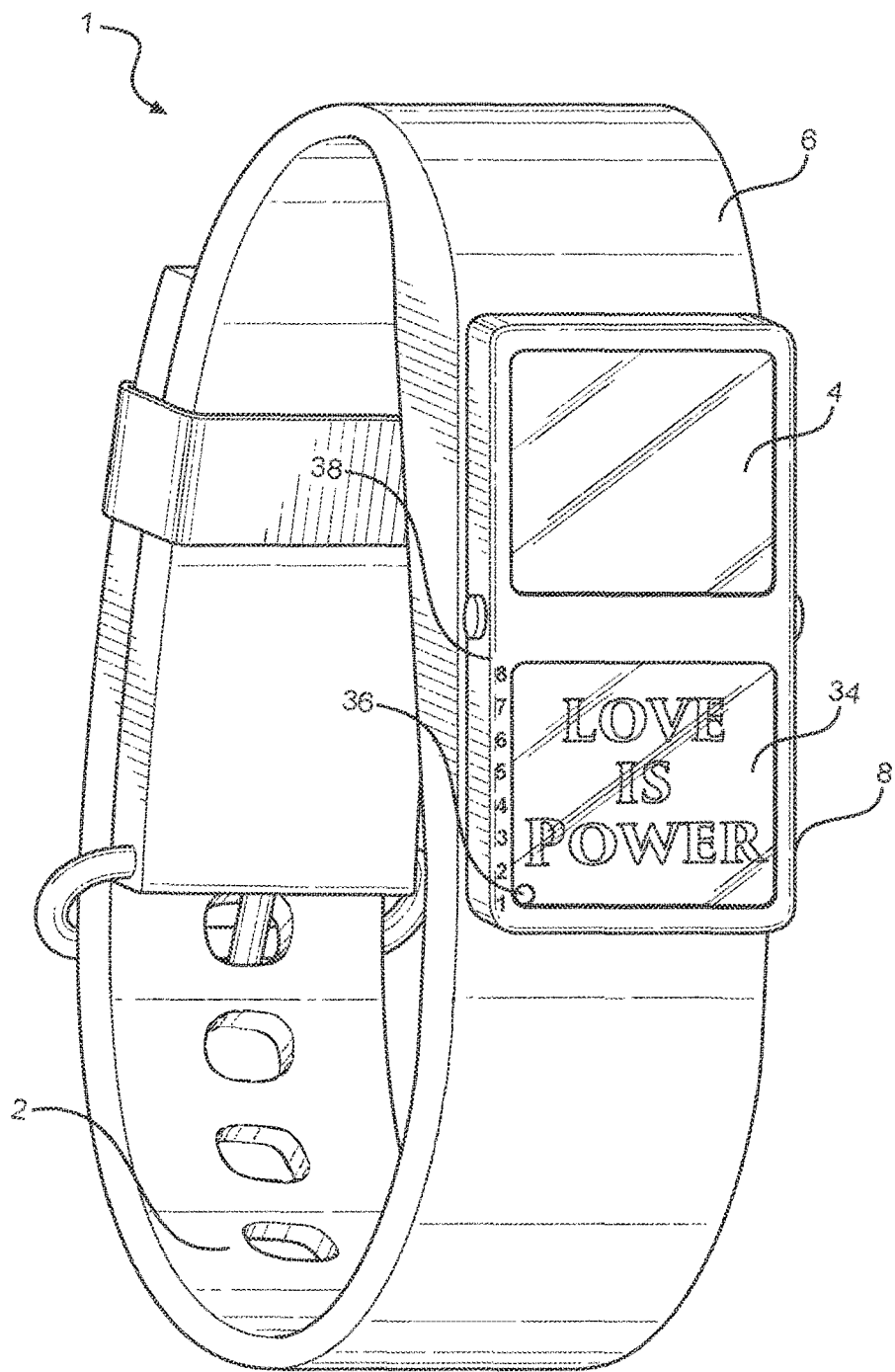
FIG. 2 is a perspective view illustrating an athletic tracking device with the handle member down and showing a different motivational image according to an embodiment of the present invention of FIG. 1.

For the band version of the athletic tracking device 1, as seen in FIGS. 1 and 2, the photo image 10 (FIG. 1) is gradually revealed as the user pushes the front cover member 34 (FIG. 2) back one ridge 38 (FIG. 1) at a time as one slowly reaches their goal in order to reveal the "full" power photo image 10 (FIG. 1) that is helping them stay motivated. A knob exists 36 (FIG. 2) exists that can be leveraged for pushing the front cover member 34 (FIG. 2) up or back down.

The Power Pic—"Power Surge":

For the watch version of the athletic tracking device 1, as seen in FIG. 3, when a person needs an extra inspirational boost of power, then they could request to see a uniquely dedicated photo, video, or message image 10 which could be known as a "Surge", that is set up specifically via the app for days when an extra surge of motivation is needed.

Custom Mantra:

For the watch version of the athletic tracking device 1, as seen in FIG. 3, a customized mantra can also be displayed as an image 10 constantly to keep one motivated. The mantra can be selected from a list of common motivational mantras or personally created using the app. Users would be able to choose the color and the font used for the words. For the band version of the athletic tracking device 1, as seen in FIG. 2, the mantra would be engraved on the front cover member 34.

The App:

For the watch version of the athletic tracking device 1, as seen in FIG. 3, using the app, users will be able to customize their goals just like other sport/fit watches. These would be tracked automatically using a pedometer 24 for monitoring the number of steps, a heart rate monitor 22, and an elevation monitor 20 for monitoring the number of flights of stairs that are climbed within a set time period.

Power Pic "Friend Grid":

For the watch version of the athletic tracking device 1, as seen in FIG. 3, friend Power Pics, videos, or message images 10 can be uploaded and displayed/sent to friends to be revealed once a friend achieves his or her goals or when one achieves their own goal and wants to share their success with friends. Also Power Pic "Surges" (photos, videos, or message images 10) can be sent to friends to motivate them to accomplish their goals. Group competitions would allow for Power Photos, videos, or message images 10 to be shared when the individual members of the group as each member reaches their goal and/or only when everyone in the group reaches their goals (multiple options). These options can be set up via the app. The Power Pic supports a "Power Grid" of friends to help each other surge on.

Power Pic "Community Sponsor Grid":

For the watch version of the athletic tracking device 1, as seen in FIG. 3, a powerful "grid" of companies could sponsor this fitness movement by offering rewards, such as coupons or prizes for certain health goal milestones. For example, if an individual walks over 100 miles in a month, a company would unlock a surprise gift photo, video or voice message image 10. It could be a coupon for saving money when making a purchase or a free gift, like a pair of running socks, sun block, sunglasses, etc. This surprise picture, video or voice message image 10 would have a barcode or coupon code that can be scanned or entered when claiming the prizes. Sponsoring businesses would set up the community goals via the Community Sponsorship Grid App, which would be a separate app for businesses to utilize. Individuals from the community would register for the sponsored goals using the Power Pic App.

For the watch version of the athletic tracking device 1, as seen in FIG. 3, sponsoring businesses can establish the goals via the Community Sponsorship Grid App, where they can set up the goals and related prizes or rewards for accomplishing the goals. The goals the sponsor would set up might be walking so many miles a month or so many miles per year, etc. The app would have standard choices, such as expiration dates, number of uses for gifts/coupons, etc." This would be a "grid" of businesses helping to support health in the community by helping people find the power to reach their goals.

Power Pic "Sponsor Fundraising Grid":

For the watch version of the athletic tracking device 1, as seen in FIG. 3, various businesses together would create a virtual "Power Grid" by raising funds and creating "power in the community" to improve health. For example, a sponsor may agree to donate $10 to the American Cancer Society or a community walking trail for every person that walks one hundred miles within a specified time period. As a person using this device and app meets these goals, a related inspirational Power photo or video image 10 of the walking trail or maybe a young girl that has beat cancer can be displayed as inspiration. As part of the business/sponsorship fund raising or goal program, positive messages, advice, awareness, recommendations, and facts related to the fundraising event of goal will be shared to provide needed motivation. For example, when raising funds for an American Cancer Society event, when a user is 25% of the way towards the goal, a surprise pop-up photo, video, or voice message image 10 relating the fact that meditating for five minutes daily may help to decrease a person's changes of getting cancer can be displayed.

The Band Version:

The band version of the athletic tracking device 1, as seen in FIGS. 1 and 2, would be much simpler, with no automation. A Power photo image 10 (FIG. 1) would be hidden under a front cover member 34 (FIG. 2) which the user slides back slowly, one ridge 38 (FIG. 1) at a time as they work towards their goals, to reveal it. The front cover member 34 (FIG. 2) would have a mantra engraved on it for some extra inspiration. The front cover member 34 (FIG. 2) would likely slide under the part of the band where the logo is displayed. The photo image 10 (FIG. 1) would be added manually and is sealed to prevent it being damaged by moisture or perspiration. Individuals would choose a band with the appropriate number of ridges 38 (FIG. 1) on it that matches their individual goal. For example, if an individual is tracking the number of glasses of water he/she wants to drink a day, they would choose the wrist band 2 (FIG. 1) with eight ridges 38 (FIG. 1). If the individual wanted to complete ten sets of ten exercises a day, they would choose a wrist band 2 (FIG. 1) with ten notches. The band version would be much less expensive to purchase than any of the watch versions. A website could exist for an individual to choose the color, the number of ridges 38 (FIG. 1), and the personalized mantra to be engraved on the front cover member 34 (FIG. 2). Bands 2 with common popular mantras and a typical number of ridges 38 (FIG. 1) in various colors could also be sold.

Slider/Button Only Band:

Another version of the athletic tracking device band (not pictured) would have one to four sliding trackers (like 8 as seen in FIG. 3) or buttons with a printed photo/icon image (like the water droplet goal icon 18 as seen in FIG. 3) of what is being tracked or the color of the band may represent what is being tracked, such as a blue band for tracking number of glasses of water. For example, one tracker/slider would have an icon of a "water droplet" to track the number of glasses of water consumed daily. Another slider/tracker would have an icon of piece of fruit to track the number of fruits consumed daily. Other trackers/sliders could be for tracking the number of veggies consumed daily (with an icon of a vegetable), or maybe the number of meditation breaks during the day (with an icon that stands for breathing or yoga). One band may only have a counter on it and be blue to represent that the user is tracking the number of glasses of water consumed. The possibilities of the various sliding trackers are endless. One version of the bands could be similar to collection of bangles (thin bands) and the user may have one bangle band for tracking water, another for tracking veggies, and the last one for tracking meditation breaks during the day, etc. User will be able to track their exercise, water, food, good deeds, miles, number of daily breaks or anything. A website would be used to select popular bands with "standard" slider/button trackers on them or users could create a custom band by choosing from an existing list of various slider trackers/buttons and band colors and designs. Lastly, they could also upload their own icon and choose the number of notches. This version would not have a personalized photo, but a printed on icon image of what the user wants to track. No one enjoys logging into their phone and digging way down into an app fifteen times a day to track their progress. These trackers will make it easy for individuals to track what is important to them. In addition, on the watch version, which has fruit and veggie trackers, the users could choose something different than the fruit and veggies trackers. The slider can be reset to zero by moving it back down to zero. The button could be reset to zero by holding down the button for a short period of time.

The athletic tracking device 1, as seen in FIG. 3, has a wrist band 2 which is adapted to releasably attach the athletic tracking device 1 to a user's wrist. The athletic tracking device 1 also has a tracking unit 28 attached to the wrist band 2 which includes a main body 6 having a front panel portion 4 which is adapted to display one or more images 10. The images 10 are adapted to be individually and removably placed upon the front panel portion 4 depending on a chosen fitness goal. The tracking unit 28 is attached to the wrist band (like 2 in FIG. 2). The tracking unit 28 has interior volume and a computer member 14 which is located within the tracking unit 28 and is electronically connected to the front panel portion 4. The computer member 14 includes software applications adapted to track and provide information pertaining to fitness goals determined by the user. The front panel portion 4 may be a touchscreen enabling the user to select options relating to personalized fitness goals; wherein, said touch screen is configured to receive an electrical impulse from the touch of a user to input information relating to personalized fitness goals and to send that information to the computer member for analysis.

The athletic tracking device 1 as seen in FIG. 3, the computer member 14 is also adapted to provide portions of an image 10 to be displayed upon the front panel portion 4 depending upon the progress of the user reaching a chosen fitness goal. The tracking unit 28 further includes a speaker member 16 electronically attached to the computer member 14 and is adapted to emit audio sounds depending on the progress of the user reaching a chosen fitness goal.

The athletic tracking device 1 as seen in FIG. 3, the images 10 to be displayed upon the front panel portion 4 includes video images and/or text messages as desired by the user. The tracking unit 28 further includes a pedometer 24 electronically attached to the computer member 14 and is adapted to count the number of steps a user has taken during a chosen period of time and to send that information to the computer member 14 for analysis and display on the front panel portion 4.

The athletic tracking device 1 as seen in FIG. 3, the tracking unit 28 further includes a microphone member (not diagramed) electronically attached to the computer member 14 and is adapted to receive audio sounds to be stored and used by the computer member 14. These audio sounds are adapted to be emitted by the speaker member 16 depending upon the progress of the user reaching a chosen fitness goal.

The athletic tracking device 1 as seen in FIG. 3, the tracking unit 28 also includes a heart rate monitor 22. The heart rate monitor 22 is also electronically attached to the computer member 14 and is adapted to monitor the heart rate of a user during a chosen period of time and to send that information to the computer member 14 for analysis and display on the front panel portion 8.

The athletic tracking device 1 as seen in FIG. 3, an elevation monitor is also included in the tracking unit 28 and is attached to the computer member 14 and is adapted to determine the elevation above sea level which the athletic tracking device 1 is located and to send that information to the computer member 14 for analysis and display on the front panel portion 8. The tracking unit 28 also includes a receiver 26 electronically attached to the computer member 14 and is adapted to receive electronic signals and a transmitter (not diagrammed) electronically attached to the computer member 14 adapted to send electronic signals such that the athletic tracking device 1 is adapted to communicate remotely with other computer systems.

The athletic tracking device 1 as seen in FIG. 3, is adapted to receive information from companies and sponsors offering coupons and prizes for reaching chosen athletic goals. That information includes barcodes adapted to be displayed on the front panel portion 4 and used to retrieve the prizes from a merchant in possession of them.

Figure 5:
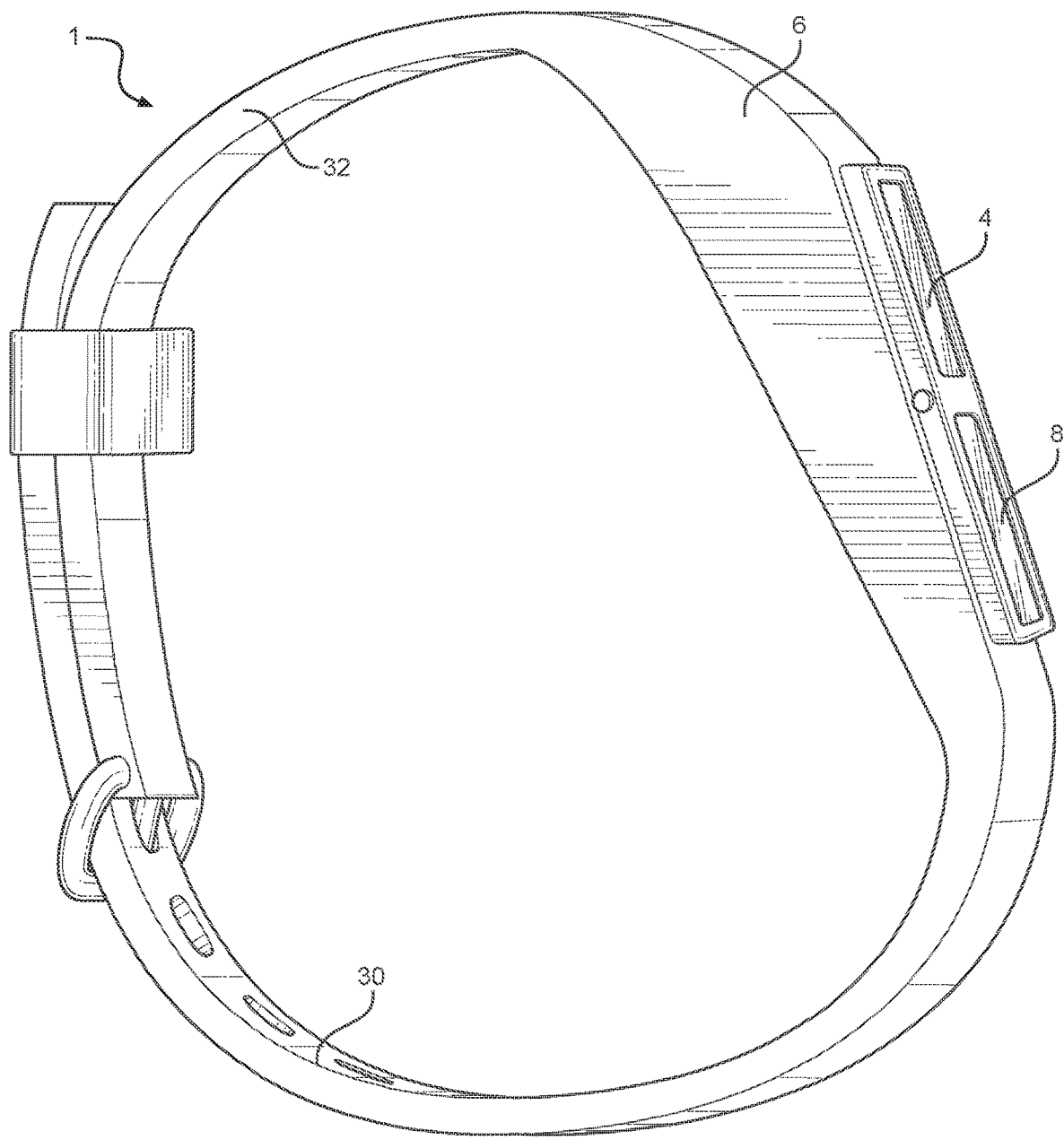
FIG. 5 is a side view of an athletic tracking device according to an embodiment of the present invention of FIG. 1.
Figure 6:
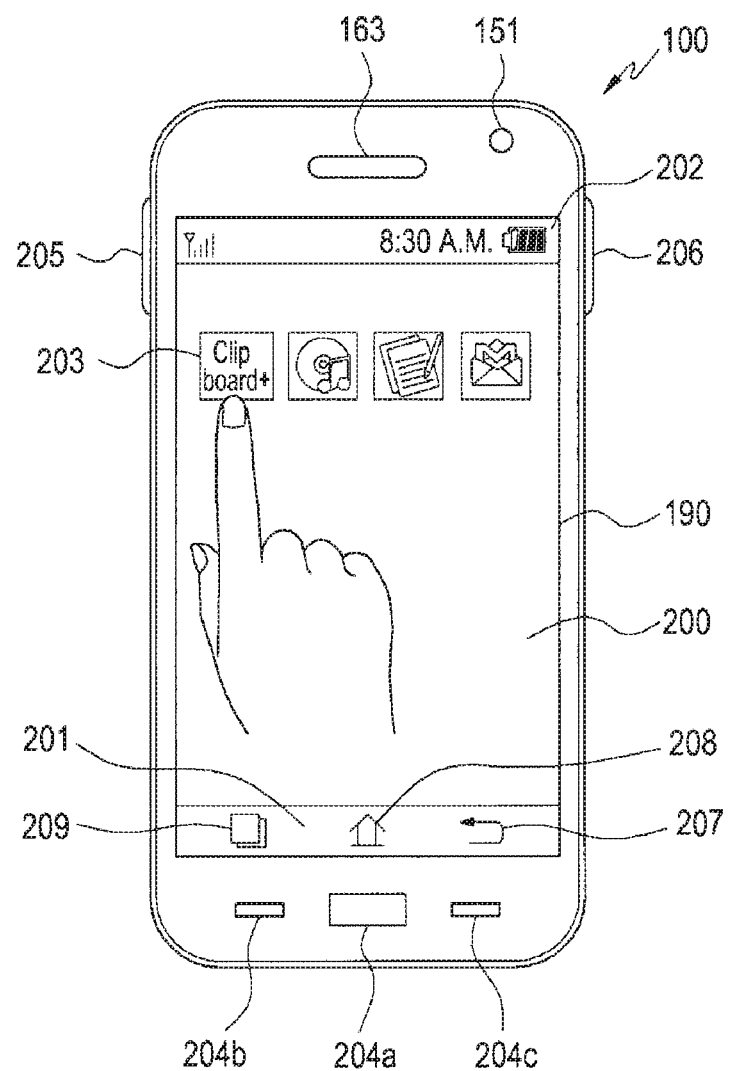
FIG. 6 is a front view of an athletic tracking device according to the preferred embodiment of the present invention.
Figure 7:
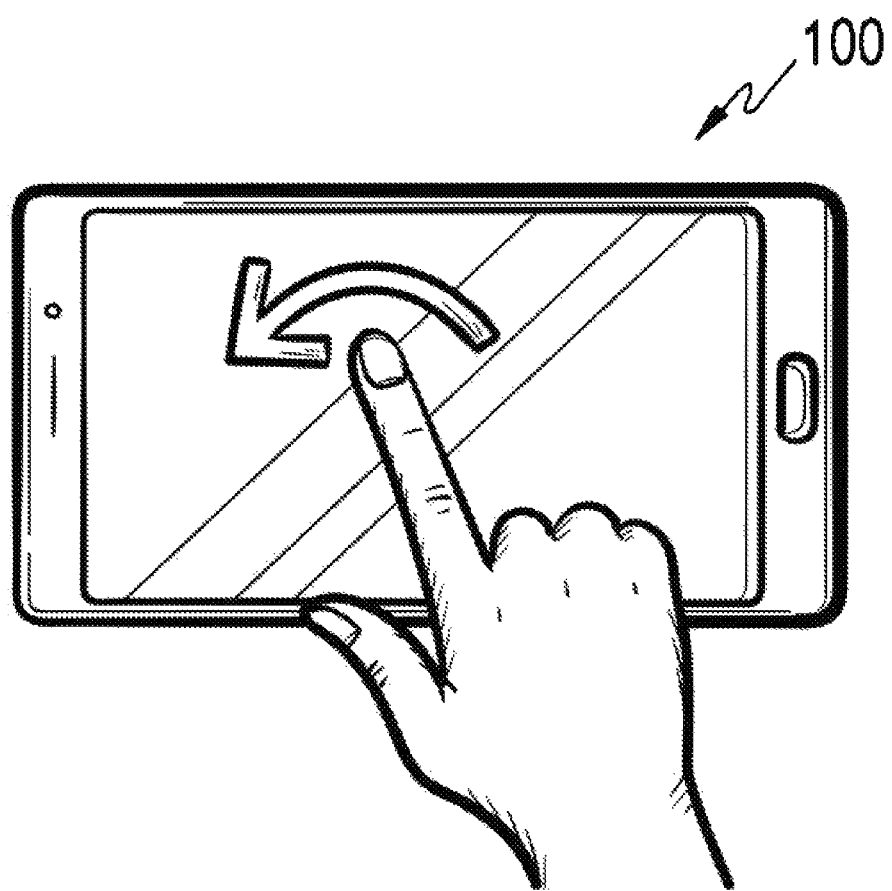
FIG. 7 is a front view of an athletic tracking device showing touch screen capabilities according to the preferred embodiment of the present invention of FIG. 6.
Figure 8:
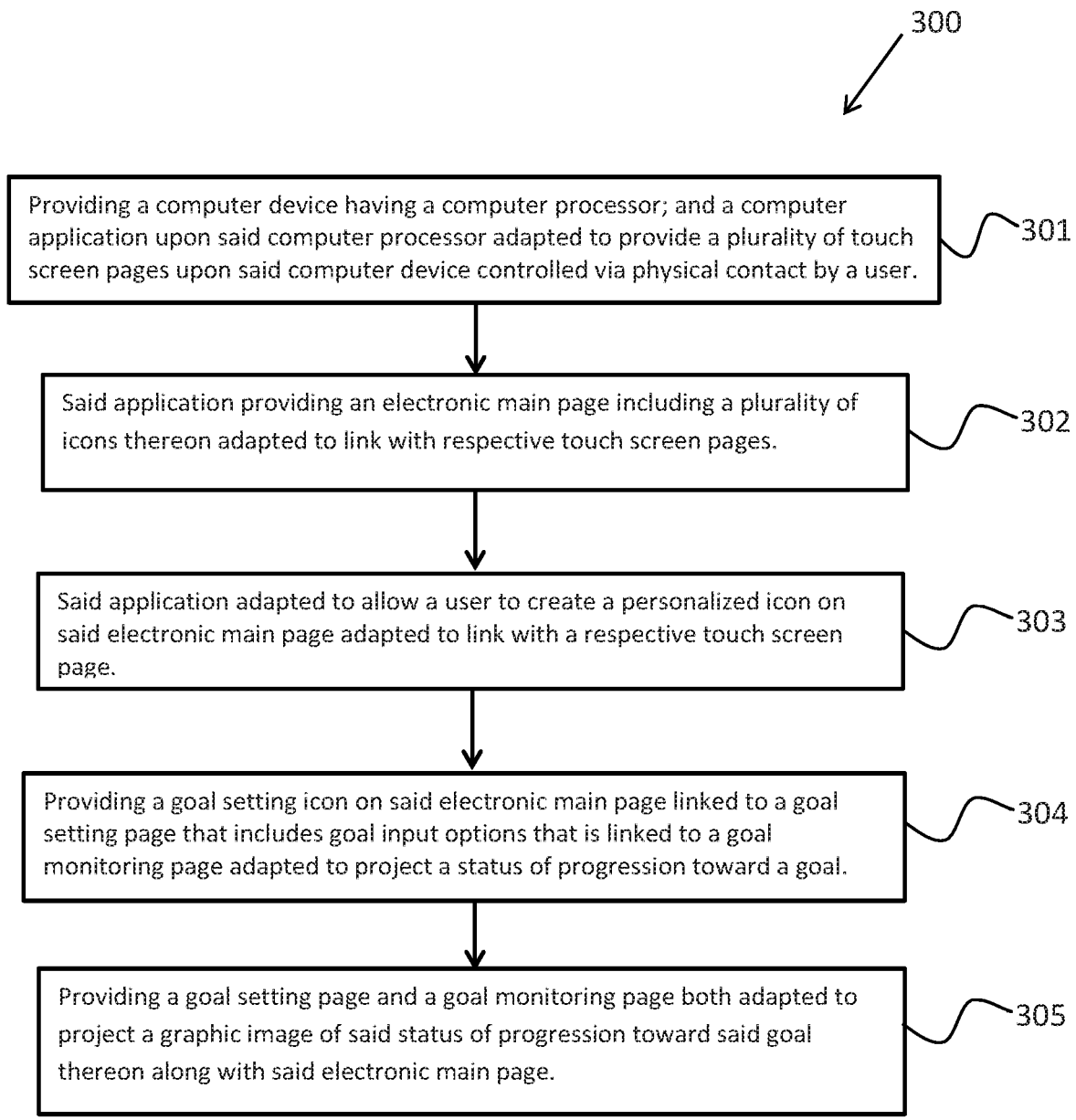
FIG. 8 is a flow chart showing a method of tracking and incentivizing personal goals using the athletic tracking device according to the preferred embodiment of the present invention of FIG. 6.
Figure 9:
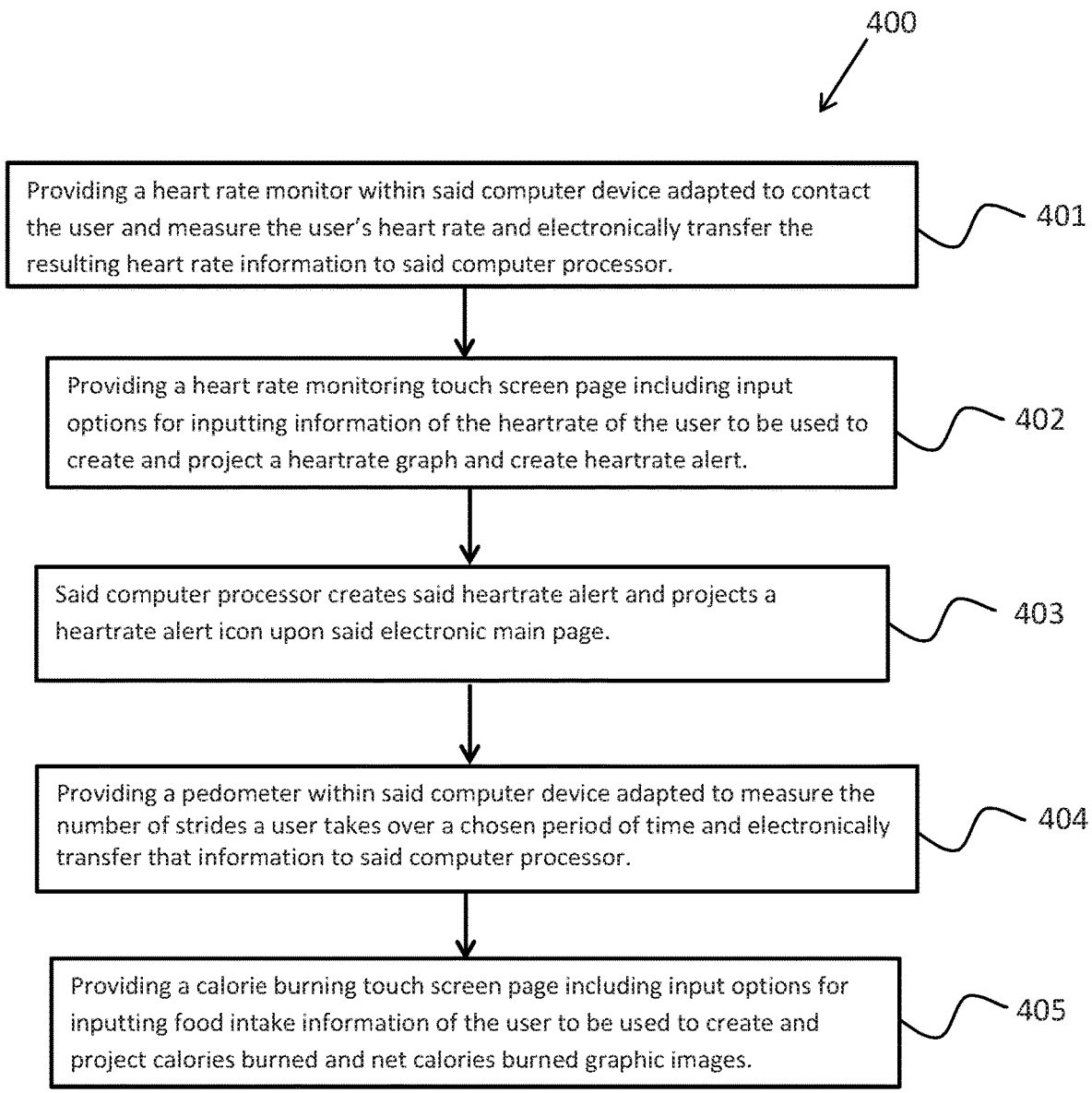
FIG. 9 is a flow chart showing a furtherance of the method of tracking and incentivizing personal goals using the athletic tracking device shown in FIG. 8.

The athletic tracking device 1 as seen in FIGS. 2 and 5, the wrist band 2 (FIG. 2) of the athletic tracking device 1 (FIG. 5) has a first strap portion 30 (FIG. 5) attached to one side of the main body 6 (FIG. 5) and a second strap portion 32 (FIG. 5) attached to the opposite side of the main body 6 (FIG. 5). An end portion of the second strap portion 32 (FIG. 5) is removably attached to an end portion of the first strap portion 30 (FIG. 5) such that the athletic tracking device 1 (FIG. 5) is adapted to be removably and securely attached to the wrist of a user.

The athletic tracking device 1 as seen in FIG. 2, athletic tracking device 1 also includes a front cover member 34, adapted to be movably connected to the main body 6 and to selectively cover the front panel portion 4 depending upon a user reaching a chosen fitness goal. The front cover member 34 includes a handle member 36 which allows the user to slide the front cover member 34 with respect to the front panel portion 4 to reveal a chosen printed image in stages depending on the progress of a user reaching a chosen fitness goal.

The athletic tracking device 1 as seen in FIGS. 1 and 2, has a main body 6 (FIG. 1) further includes a plurality of ridges 38 (FIG. 1) adapted to removably retain the handle member 36 (FIG. 1) in predetermined locations to allow the user to slide the front cover member 34 (FIG. 2) with respect to the front panel portion 4 (FIG. 2) and reveal a chosen printed image 10 in stages depending on the progress of a user reaching a chosen fitness goal.

In the preferred embodiment, illustrated in FIGS. 6-9, a smart phone or device 100 is used to provide a method of tracking and incentivizing personal goals 300 comprises a step 301 of providing a computer device 100 including at least one computer processor, and an electronic touch screen 190 wherein the electronic touch screen is electronically connected to the computer processor and is adapted to be controlled via physical contact by a user, and of providing a computer application encoded onto the computer processor, wherein the computer application provides a plurality of electronic touch screen pages adapted to be displayed upon the electronic touch screen 190, and wherein the pages can be changed, chosen, and moved via physical contact by the user, i.e., via their finger, upon the electronic touch screen 190; a step 302 to provide an electronic main page 200 that may include a plurality of icons 203 thereon, wherein each of the plurality of icons is respectively linked to one of the plurality of electronic touch screen pages when the icon is chosen via physical contact by the user; a step 303 to provide an input option to create at least one personalized icon 203 upon said electronic main page, wherein each of the personalized icons are respectively linked to one of the electronic touch screen pages when the personalized icon is chosen via physical contact by the user; a step 304 wherein at least one of the personalized icons is a goal setting icon respectively linked to a respective goal setting electronic touch screen page, providing a goal setting electronic touch screen page including electronic input options including inputting a title for a goal, inputting values for the goal, an option to save the goal and its title and associated values and create a goal monitoring electronic touch screen page for the goal and its title and associated values, and an option to revert back to the electronic main page; and a step 305 to provide at least one goal monitoring electronic touch screen page including a graphic image providing the title of the respective goal, a graphic image providing the values of the respective goal, at least one data input function, wherein the data input function allows a user to input data correlating to the progression toward the respective goal, providing a graphic image illustrating the percent of completion of a respective goal, and an option to project the graphic images of the title and the percent of completion of the respective goal upon the electronic main page.

The graphic image of the percent of completion of the respective goal may be formed as a pound sign "#", wherein each line of the pound sign is adapted to be projected as a different color representing the progression toward the goal. The colors representing the progression toward the goal can be red (not near the goal), yellow (near the goal), and green (goal achieved) or other color patters such as a light color (not near the goal), a medium color (near the goal), and a dark color (goal achieved).

The electronic input options of the goal setting electronic touch screen page may further include an input option to add a visual image that is inspirational to them, such as photographs, clip art, and videos. The values for the goal inputted within said goal setting electronic touch screen page can be adjusted. The electronic input options of the goal setting electronic touch screen page may further include an input option to create a notification to perform a task pertaining to progressing toward the goal and including an input option to input time intervals to initiate the notification, and a choice to choose between types of preset notifications including audio sounds, vibrations, and a visual images.

The computer device also includes a transceiver therein adapted to electronically connect with and communicate through an internet source; wherein the computer application further provides an option to connect with the internet source; and wherein the computer application further provides an option to share information pertaining to the progression of their goal.

As discussed previously, the electronic main page of the computer application may also include a plurality of icons 203 thereon, wherein each of the plurality of icons is respectively linked to one of the plurality of electronic touch screen pages when the icon is chosen via physical contact by the user, and wherein one of the plurality of icons is a goal setting icon linked to the goal setting electronic touch screen page, wherein the goal setting electronic touch screen page includes electronic input options including a choice between a plurality of preset goals, a choice between values of each of the preset goals, an option to save a chosen preset goal and its associated value and create a goal monitoring electronic touch screen page for that chosen preset goal and its associated value; and an option to revert back to the electronic main page; and a plurality of goal monitoring electronic touch screen pages, each including a graphic image providing a title of the chosen preset goal, a graphic image providing the values of the chosen preset goal, at least one data input function, wherein the at least one data input function allows a user to input data correlating to the progression toward the chosen preset goal, a graphic image providing the percent of completion of the chosen preset goal, and an option to project the graphic images of the title and the percent of completion of the chosen preset goal upon the electronic main page.

In the preferred embodiment, the smart phone or device 100 is used to provide further steps for the method of tracking and incentivizing personal goals 400 comprising a step 401 providing a heart rate monitor 22 adapted to contact the user and measure the user's heart rate and electronically transfer the resulting heart rate information to the computer processor; and wherein an electronic main page is created including an option to project a graphic image providing the heart rate information of the user upon the electronic main page. The computer application would further provide a step 402 which creates a heart monitoring touch screen page including a resting heartrate input function which would allow a user to input data correlating to their normal resting heartrate; and a heart rate graph including a time parameter, a beats per minute parameter, and a resting heartrate overlay, wherein the heart rate graph is adapted to project heart rate information over a chosen period of time, including real time; and a step 403 which creates a heart rate alert in the form of a flashing heart-shaped icon on the heart monitoring touch screen page and the electronic main page.

In the preferred embodiment, the smart phone or device 100 is used to provide further steps for the method of tracking and incentivizing personal goals 400 comprising a step 404 providing a pedometer 24 adapted to measure the number of strides a user takes over a chosen time period and send that information to the computer processor; and wherein the electronic main page would further includes an option to project a graphic image providing the pedometer information of the user upon the electronic main page. And a step 405 wherein the computer application would further create a calorie burning touch screen page including a food intake input function that would allow a user to input information about food ingested over a chosen time period, wherein the information about the food ingested is electronically sent to the computer processor, and wherein the computer processor determines the number of calories ingested; a calories burned graphic image adapted to display the number of calories burned computed by the computer processor using the information from the pedometer; and a net calories graphic image adapted to display the number of net calories computed by the computer processor using the information from the pedometer and the food intake input information.

Important features of the instant invention further include directly counting/tracking items directly on the device main screen itself. All other fitness devices require you to "log into an app" and count how many, for example, glasses of water or servings of food on the app, which takes a lot of extra steps. The instant invention lets you quickly count items directly on the device main screen with a swipe or two and then tapping. No need to log into a phone at all.

The instant invention lets you "customize" your item or goal and create your "very own item" to count/track directly on the device. You can create your very own item to track, such as tracking "walking the dog". You would type in "dog" and set your goal to a value, such as "2". Then after walking the dog, you bring up your device, swipe to dog, and tap to indicate you completed the task. Later that day you can do it again.

The instant invention helps people remember if they completed a task or not. One item you can choose on the device is "prescription" or "vitamins". Once you take your prescription or vitamin you count that on your device and "remember" if you took your pill or not. One can even track/count "bad habits" like smoking, soda, sugar, etc. On this device, you can keep track of how many smoke breaks you take a day without having to log into your phone and try to reduce it and improve your health.

The instant invention further provides a "Grade Card System" that "reports your results" in an "old school" grade card way reporting where if you hit your goals 90% of the time, you get an A, 80% of the time is B, etc. These "grades" can be reported to the user and to outside entities, like Facebook or various companies for future uses, like rewards, company discounts, etc. These grades can be reported over specified time periods, like a quarter, trimester, year. The grading system can be used in "group goals", such as a team of users all encouraging one another to get A's and B's, etc. Also used in reward systems, such as prizes for A's, etc.

The instant invention would have a "custom tags" communication feature where the user could create custom announcements related to accomplishments. The user could choose from a set of common taglines, like "Nailed it #", "Slayed It #", "Shredded #", "Pushed Thru #" or create their own tagline and share their accomplishment or the progress of their accomplishment on social media. Group goal taglines may be created, such as "30 Pushups—Nailed it #" so that if in a group competition, the user could choose share a status in order to encourage others to "Nail it" as well. The custom tags would be shared along with the pound sign that has the colors that indicates status. The colors on the pound side, are typically red, yellow, green, but, could be customized to different colors, likely a light, medium and a dark and/or fluorescent color to indicate status. For example during breast cancer awareness month, the colors maybe light pink, a medium pink (close to goal) and a fluorescent pink (goal met).

The instant invention further would be have the ability to share the collected users data with other entities, like healthcare companies, businesses, apps, etc. with the users' consent in order for the user to participate in various accomplishing goals reward systems, such as healthcare discounts, prizes and more.

The instant invention would have an "easy interval" feature where the user could create and name custom interval workouts by specifying the number of intervals for the workout and how long each interval would last. For example, the user may create an "easy interval" workout called "Track Workout" and set 3 intervals, where the $1^{st}$ interval is for 1 minute, the $2^{nd}$ interval is for 30 seconds and the $3^{rd}$ interval is for 2 minutes. The user may use their custom "Track Workout" to jog for 1 minute, run for 30 seconds and walk for 2 minutes. The user could create multiple "easy interval" workouts and choose which one they want to set on the watch before their daily workout.

The four lines of the pound sign "#" turn from red to yellow to green as you get close to your "healthy goal", or they can turn from green to yellow to red if you don't stay under your goal count for your "unhealthy goal" (i.e., smoking).

The instant invention further provides for competitions that users can join where "companies" sponsor a competition to help raise money for charities if you join the competition and reach your goal.

The application of the instant invention may be updated over the internet and be adapted to be used in both Android and iOS systems.

When a user first uses the device of the instant invention, the application will have a preloaded list of around twenty to thirty icons on the main page that the user can use to track items. They will be able to choose up to four items to track. If they want to track something that doesn't have a preloaded icon they are given the option to enter a word (up to a certain number of characters, such as maybe eight characters). They can also re-arrange the icons in order of importance. This can also be used to determine which pages appear on the device as well as which item is depicted in the center of a tracking tab. In some embodiments, to get to a goal entry page there should be a "Set Goals" button on a counting page. The goal entry page may have twenty to thirty pre-loaded icons. Each icon will also have a default value. The user can see the history of each of the four tracking icons they chose. The user will also be able to create a notification to drink water. This notification will work similar to the inactivity notification that's currently on the device and app. The user will input into the app how often they want to be reminded if they haven't tracked water in that given amount of time. The user will also be able to set the time of day to turn the notification "on". If the user puts in 8 am to 9 pm and wants to be reminded every hour this is the screen that would show up on the device if the user hadn't tracked any water in the past hour. This screen would also be accompanied by a vibration. This may also include a Healthy Snack or Break Notification and any additional notifications the goals/icons on the invention.

In other possible embodiments, the instant invention may have a camera that records what a person is physical doing, like drinking water or smoking a cigarette, and the software on the device be adapted to "interpret" and track those events.

Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A method of tracking and incentivizing personal goals comprising the steps of:
providing a computer device including:
at least one computer processor; and
an electronic touch screen;
wherein said electronic touch screen is electronically connected to said computer processor and is adapted to be controlled via physical contact by a user;
providing a computer application encoded onto said computer processor, wherein said computer application provides:
a plurality of electronic touch screen pages:
wherein said plurality of electronic touch screen pages are adapted to be displayed upon said electronic touch screen, wherein said pages can be changed, chosen, and moved via physical contact by said user upon said electronic touch screen;
an electronic main page including:
an input option to create at least one personalized icon thereon;
wherein each of said at least one personalized icon is respectively linked to one of said plurality of electronic touch screen pages when said at least one personalized icon is chosen via physical contact by said user;
wherein each of said at least one personalized icon are goal setting icons respectively linked to a goal setting electronic touch screen page;
a goal setting electronic touch screen page including:
electronic input options including:
inputting a title for a goal;
inputting values for said goal;
an option to save said goal and its title and associated values and create a goal monitoring electronic touch screen page for said goal and its title and associated values; and
an option to revert back to said electronic main page; and
at least one goal monitoring electronic touch screen page including:
a graphic image providing said title of said respective goal;
a graphic image providing said values of said respective goal;
at least one data input function;
wherein said at least one data input function allows a user to input data correlating to the progression toward said respective goal;

a graphic image providing the percent of completion of said respective goal; and
an option to project said graphic images of said title and said percent of completion of said respective goal upon said electronic main page.

2. The method of tracking and incentivizing personal goals of claim 1, wherein said graphic image of said percent of completion of said respective goal is formed as a pound sign (#); and wherein each line of said pound sign is adapted to be projected as a different color representing the progression toward said goal.

3. The method of tracking and incentivizing personal goals of claim 2, wherein said colors representing the progression toward said goal are chosen from a list of colors consisting of red (not near goal), yellow (near goal), and green (goal met); and wherein patterns are used to represent the progression toward said goal; wherein said patterns are chosen from a list of patterns consisting of light colors (not near goal), medium colors (near goal), and dark colors (goal met).

4. The method of tracking and incentivizing personal goals of claim 1, wherein said electronic input options of said goal setting electronic touch screen page further includes an input option to add a visual image that is inspirational to them chosen from a group of inspirational images consisting of photographs, clip art, and videos.

5. The method of tracking and incentivizing personal goals of claim 1, wherein said values for said goal inputted within said goal setting electronic touch screen page is adjustable.

6. The method of tracking and incentivizing personal goals of claim 1, wherein said electronic input options of said goal setting electronic touch screen page further includes an input option to create a notification to perform a task pertaining to progressing toward said goal.

7. The method of tracking and incentivizing personal goals of claim 6, wherein said input option to create a notification includes an input option to input time intervals to initiate said notification, and a choice to choose between types of preset notifications.

8. The method of tracking and incentivizing personal goals of claim 7, wherein said types of preset notifications are chosen between a list of preset notifications consisting of an audio sound, a vibration, and a visual image.

9. The method of tracking and incentivizing personal goals of claim 1, wherein said computer device includes a transceiver adapted to electronically connect with and communicate through an internet source; wherein said computer application further provides an option to connect with said internet source; and wherein said computer application further provides an option to share information pertaining to the progression of their goal.

10. A method of tracking and incentivizing personal goals comprising the steps of:
providing a computer device including:
at least one computer processor; and
an electronic touch screen;
wherein said electronic touch screen is electronically connected to said computer processor and is adapted to be controlled via physical contact by a user;
providing a computer application encoded onto said computer processor, wherein said computer application provides:
a plurality of electronic touch screen pages:
wherein said plurality of electronic touch screen pages are adapted to be displayed upon said electronic touch screen, wherein said pages can be changed, chosen, and moved via physical contact by said user upon said electronic touch screen;
an electronic main page including:
a plurality of icons thereon;
wherein each of said plurality of icons is respectively linked to one of said plurality of electronic touch screen pages when said icon is chosen via physical contact by said user;
wherein one of said plurality of icons is a goal setting icon linked to a goal setting electronic touch screen page;
a goal setting electronic touch screen page including:
electronic input options including:
a choice between a plurality of preset goals;
a choice between values of each of said preset goals;
an option to save a chosen preset goal and its associated value and create a goal monitoring electronic touch screen page for that chosen preset goal and its associated value; and
an option to revert back to said electronic main page; and
a plurality of goal monitoring electronic touch screen pages, each including:
a graphic image providing a title of said chosen preset goal;
a graphic image providing said values of said chosen preset goal;
at least one data input function;
wherein said at least one data input function allows a user to input data correlating to the progression toward said chosen preset goal;
a graphic image providing the percent of completion of said chosen preset goal; and
an option to project said graphic images of said title and said percent of completion of said chosen preset goal upon said electronic main page.

11. The method of tracking and incentivizing personal goals of claim 10, wherein said computer device further comprises:
a heart rate monitor;
wherein said heart rate monitor is adapted to contact the user and measure the user's heart rate and electronically transfer the resulting heart rate information to said computer processor; and
wherein said electronic main page further includes:
an option to project a graphic image providing the heart rate information of said user upon said electronic main page.

12. The method of tracking and incentivizing personal goals of claim 11, wherein said computer application further provides:
a heart monitoring touch screen page including:
a resting heartrate input function;
wherein said resting heartrate input function allows a user to input data correlating to their normal resting heartrate; and
a heart rate graph including:
a time parameter; and
a beats per minute parameter; and
a resting heartrate overlay;
wherein said heart rate graph is adapted to project heart rate information over a chosen period of time, including real time; and a heart rate alert;
   wherein said heart rate alert is in the form of a flashing heart-shaped icon on said heart monitoring touch screen page and said electronic main page.

13. The method of tracking and incentivizing personal goals of claim 10, wherein said computer device further comprises:
   a pedometer;
      wherein said pedometer is adapted to measure the number of strides a user takes over a chosen time period and send that information to said computer processor; and
   wherein said electronic main page further includes:
      an option to project a graphic image providing the pedometer information of said user upon said electronic main page.

14. The method of tracking and incentivizing personal goals of claim 13, wherein said computer application further provides:
   a calorie burning touch screen page including:
      a food intake input function;
         wherein said food intake input function allows a user to input information about food ingested over a chosen time period;
         wherein said information about said food ingested is electronically sent to said computer processor; and
         wherein said computer processor determines the number of calories ingested; and
      a calories burned graphic image;
         wherein said calories burned graphic image is adapted to display the number of calories burned computed by said computer processor using said information from said pedometer; and
      a net calories graphic image;
         wherein said net calories graphic image is adapted to display the number of net calories computed by said computer processor using said information from said pedometer and said food intake input information.

15. The method of tracking and incentivizing personal goals of claim 10, wherein said values for said goal inputted within said goal setting electronic touch screen page is adjustable.

16. The method of tracking and incentivizing personal goals of claim 10, wherein said electronic input options of said goal setting electronic touch screen page further includes an input option to create a notification to perform a task pertaining to progressing toward a respective preset goal.

17. The method of tracking and incentivizing personal goals of claim 16, wherein said input option to create a notification includes an input option to input time intervals to initiate said notification, and a choice to choose between types of preset notifications.

18. The method of tracking and incentivizing personal goals of claim 17, wherein said types of preset notifications are chosen between a list of preset notifications consisting of an audio sound, a vibration, and a visual image.

19. The method of tracking and incentivizing personal goals of claim 10, wherein said computer device includes a transceiver adapted to electronically connect with and communicate through an internet source; wherein said computer application further provides an option to connect with said internet source; and wherein said computer application further provides an option to share information pertaining to the progression of each respective preset goal.

20. A method of tracking and incentivizing personal goals comprising the steps of:
   providing a computer device including:
      at least one computer processor; and
      an electronic touch screen;
         wherein said electronic touch screen is electronically connected to said computer processor and is adapted to be controlled via physical contact by a user;
   providing a computer application encoded onto said computer processor, wherein said computer application provides:
      a plurality of electronic touch screen pages:
         wherein said plurality of electronic touch screen pages are adapted to be displayed upon said electronic touch screen, wherein said pages can be changed, chosen, and moved via physical contact by said user upon said electronic touch screen;
      an electronic main page including:
         a plurality of icons thereon;
            wherein each of said plurality of icons is respectively linked to one of said plurality of electronic touch screen pages when said icon is chosen via physical contact by said user;
            wherein one of said plurality of icons is a goal setting icon linked to a goal setting electronic touch screen page; and
         an input option to create at least one personalized icon thereon;
            wherein each of said at least one personalized icon are respectively linked to one of said plurality of electronic touch screen pages when said at least one personalized icon is chosen via physical contact by said user;
            wherein each of said at least one personalized icon are goal setting icons respectively linked to a goal setting electronic touch screen page;
      a goal setting electronic touch screen page including:
         electronic input options including:
            a choice between a plurality of preset goals;
            a choice between values of each of said preset goals;
            an option to save a chosen preset goal and its associated value and create a goal monitoring electronic touch screen page for that chosen preset goal and its associated value; and
            an option to revert back to said electronic main page; and
      a plurality of goal monitoring electronic touch screen pages, each including:
         a graphic image providing a title of said chosen preset goal;
         a graphic image providing said values of said chosen preset goal;
         at least one data input function;
            wherein said at least one data input function allows a user to input data correlating to the progression toward said chosen preset goal;
         a graphic image providing the percent of completion of said chosen preset goal; and
         an option to project said graphic images of said title and said percent of completion of said chosen preset goal upon said electronic main page.

* * * * *